United States Patent
Rao et al.

(10) Patent No.: US 7,833,434 B2
(45) Date of Patent: Nov. 16, 2010

(54) TETRAFLUOROPROPENE PRODUCTION PROCESSES

(75) Inventors: Velliyur Nott Mallikarjuna Rao, Wilimington, DE (US); Mario Joseph Nappa, Newark, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 127 days.

(21) Appl. No.: 12/301,077

(22) PCT Filed: Jun. 22, 2007

(86) PCT No.: PCT/US2007/014644

§ 371 (c)(1),
(2), (4) Date: Nov. 17, 2008

(87) PCT Pub. No.: WO2008/002499

PCT Pub. Date: Jan. 3, 2008

(65) Prior Publication Data

US 2009/0264689 A1    Oct. 22, 2009

Related U.S. Application Data

(60) Provisional application No. 60/816,651, filed on Jun. 27, 2006.

(51) Int. Cl.
   *C09K 5/04*    (2006.01)
   *C07C 17/25*    (2006.01)
(52) U.S. Cl. .................................. 252/67; 570/156
(58) Field of Classification Search .................. 252/67; 570/156
See application file for complete search history.

(56) References Cited

U.S. PATENT DOCUMENTS

| 6,031,141 | A | 2/2000 | Mallikarjuna et al. |
| 6,369,284 | B1 * | 4/2002 | Nappa et al. ................. 570/156 |
| 7,189,884 | B2 | 3/2007 | Mukhopadhyay et al. |
| 7,345,209 | B2 | 3/2008 | Mukhopadhyay et al. |
| 2005/0245773 | A1 * | 11/2005 | Mukhopadhyay et al. ... 570/155 |
| 2005/0245774 | A1 * | 11/2005 | Mukhopadhyay et al. ... 570/171 |
| 2006/0094911 | A1 | 5/2006 | Rao et al. |
| 2006/0106263 | A1 | 5/2006 | Miller et al. |
| 2006/0217578 | A1 * | 9/2006 | Rao et al. ..................... 570/165 |
| 2007/0179324 | A1 * | 8/2007 | Van Der Puy et al. ........ 570/156 |
| 2008/0051612 | A1 * | 2/2008 | Knapp et al. ................. 570/178 |
| 2009/0018375 | A1 * | 1/2009 | Nappa ......................... 570/156 |
| 2009/0118554 | A1 * | 5/2009 | Rao et al. ..................... 570/156 |
| 2009/0127496 | A1 | 5/2009 | Rao et al. |
| 2009/0264689 | A1 * | 10/2009 | Rao et al. ..................... 570/155 |
| 2009/0264690 | A1 * | 10/2009 | Rao et al. ..................... 570/156 |
| 2010/0032610 | A1 * | 2/2010 | Nappa et al. .................. 252/67 |

FOREIGN PATENT DOCUMENTS

| FR | 2729136 A1 | 7/1996 |
| WO | 2008002500 A1 | 1/2008 |
| WO | 2008002501 A2 | 1/2008 |

OTHER PUBLICATIONS

Morrison and Boyd, 3rd ed., Allyn and Bacon, Inc., 1973, pp. 156-159.*
CAS reg. No. 431-31-2, Nov. 16, 1984.*
CAS reg. No. 1645-83-6, Nov. 16, 1984.*
CAS reg. No. 754-12-1, Nov. 16, 1984.*

* cited by examiner

*Primary Examiner*—Douglas Mc Ginty

(57) ABSTRACT

A process is disclosed for producing 2,3,3,3-tetrafluoropropene and 1,3,3,3-tetrafluoropropene. The process involves pyrolyzing 1,1,1,2,3-pentafluoropropane.

8 Claims, No Drawings

TETRAFLUOROPROPENE PRODUCTION PROCESSES

This application represents a national filing under 35 U.S.C. 371 of International Application No. PCT/US2007/014644 filed Jun. 22, 2007, and claims priority of U.S. Provisional Application No. 60/816,651 filed Jun. 27, 2006.

FIELD OF THE INVENTION

The present invention relates to the production of tetrafluoropropenes and more specifically to the production of 2,3,3,3-tetrafluoropropene (HFC-1234yf) and 1,3,3,3-tetrafluoropropene (HFC-1234ze) from 1,1,1,2,3-pentafluoropropane (HFC-245eb).

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1234yf and HFC-1234ze, both having zero ozone depletion and low global warming potential, have been identified as potential refrigerants. U.S. Patent Publication No. 2006/0106263 A1 discloses the separate production of HFC-1234ze (mixture of E- and Z-isomers) by a catalytic vapor phase dehydrofluorination of $CF_3CH_2CHF_2$ and of HFC-1234yf by a catalytic vapor phase dehydrofluorination of $CF_3CF_2CH_3$.

There is a need for new manufacturing processes for the production both HFC-1234yf and HFC-1234ze.

SUMMARY OF THE INVENTION

The present invention provides a process comprising pyrolyzing HFC-245eb to produce HFC-1234yf and HFC-1234ze.

DETAILED DESCRIPTION

The present invention provides a process to produce both HFC-1234yf and HFC-1234ze by the pyrolysis of HFC-245eb. The reaction may be written as:

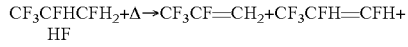

where Δ represents heat and HF is hydrogen fluoride.

HFC-245eb can be prepared by the hydrogenation of $CF_3CClFCCl_2F$ (CFC-215bb) over a palladium on carbon catalyst as disclosed in U.S. Patent Publication No. 2009/0264690, and incorporated herein in its entirety, or by the hydrogenation of $CF_3CF=CFH$ as disclosed in U.S. Pat. No. 5,396,000, incorporated herein by reference.

Pyrolysis, as the term is used herein, means chemical change produced by heating in the absence of catalyst. Pyrolysis reactors generally comprise three zones: a) a preheat zone, in which reactants are brought close to the reaction temperature; b) a reaction zone, in which reactants reach reaction temperature and are at least partially pyrolyzed, and products and any byproducts form; c) a quench zone, in which the stream exiting the reaction zone is cooled to stop the pyrolysis reaction. Laboratory-scale reactors have a reaction zone, but the preheating and quenching zones may be omitted.

The reactor for carrying out the process of the invention may be of any shape consistent with the process but is preferably a cylindrical tube, either straight or coiled. Although not critical, such reactors typically have an inner diameter of from about 1.3 to about 5.1 cm (about 0.5 to about 2 inches). Heat is applied to the outside of the tube, the chemical reaction taking place on the inside of the tube. The reactor and its associated feed lines, effluent lines and associated units should be constructed, at least as regards the surfaces exposed to the reaction reactants and products, of materials resistant to hydrogen fluoride. Typical materials of construction, well-known to the fluorination art, include stainless steels, in particular of the austenitic type, the well-known high nickel alloys, such as Monel® nickel-copper alloys, Hastelloy-based alloys and Inconel® nickel-chromium alloys and copper clad steel. Where the reactor is exposed to high temperature the reactor may be constructed of more than one material. For example, the outer surface layer of the reactor should be chosen for ability to maintain structural integrity and resist corrosion at the pyrolysis temperature, the inner surface layer of the reactor should be chosen of materials resistant to attack by, that is, inert to, the reactant and products. In the case of the present process, the product hydrogen fluoride is corrosive to certain materials. Thus, the reactor may be constructed of an outer material chosen for physical strength at high temperature and an inner material chosen for resistance to corrosion by the reactants and products under the temperature of the pyrolysis.

For the process of this invention, it is preferred that the reactor inner surface layer be made of high nickel alloy, that is an alloy containing at least about 50 wt % nickel, preferably a nickel alloy having at least about 75 wt % nickel, more preferably a nickel alloy having less than about 8 wt % chromium, still more preferably a nickel alloy having at least about 98 wt % nickel, and most preferably substantially pure nickel, such as the commercial grade known as Nickel 200. More preferable than nickel or its alloys as the material for the inner surface layer of the reactor is gold. The thickness of the inner surface layer does not substantially affect the pyrolysis and is not critical so long as the integrity of the inner surface layer is intact. The thickness of the inner surface layer is typically from about 10 to about 100 mils (0.25 to 2.5 mm). The thickness of the inner surface layer can be determined by the method of fabrication, the cost of materials, and the desired reactor life.

The reactor outer surface layer is resistant to oxidation or other corrosion and maintains sufficient strength at the reaction temperatures to keep the reaction vessel from failing of distorting. This layer is preferably Inconel® alloy, more preferably Inconel® 600.

The present pyrolysis of HFC-245eb to HFC-1234yf and HFC-1234ze and HF is carried out in the absence of catalyst in a substantially empty reactor. By absence of catalyst is meant that no material or treatment is added to the pyrolysis reactor that increases the reaction rate by reducing the activation energy of the pyrolysis process. It is understood that although surfaces that are unavoidably present in any containment vessel, such as a pyrolysis reactor, may have incidental catalytic or anticatalytic effects on the pyrolysis process, the effect makes an insignificant contribution, if any, to the pyrolysis rate. More specifically, absence of catalyst means absence of conventional catalysts in a particulate, pellet, fibrous or supported form that are useful in promoting the elimination of hydrogen fluoride from a hydrofluorocarbon (i.e., dehydrofluorination). Examples of such dehydrofluorination catalysts include: fluorided alumina, aluminum fluoride, chromium oxide, optionally containing other metals, metal oxides or metal halides; chromium fluoride, and activated carbon, optionally containing other metals, metal oxides or metal halides.

Substantially empty reactors useful for carrying out the present process are tubes comprising the aforementioned materials of construction. Substantially empty reactors include those wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, preferably in cartridge disposition for ease of insertion and removal, has an open structure like that of Raschig Rings or other packings with a high free volume, to avoid the accumulation of coke and to minimize pressure drop, and permits the free flow of gas. Preferably the exterior surface of such reactor packing comprises materials identical to those of the reactor inner surface layer; materials that do not catalyze dehydrofluorination of hydrofluorocarbons and are resistant to hydrogen fluoride. The free volume of the reaction zone is at least about 80%, preferably at least about 90%, and more preferably about 95%. The free volume is the volume of the reaction zone minus the volume of the material that makes up the reactor packing.

The pyrolysis which accomplishes the conversion of $CF_3CFHCFH_2$ to $CF_3CF=CH_2$ and $CF_3CH=CFH$ is suitably conducted at a temperature of from about 450° C. to about 900° C., preferably from about 550° C. to about 850° C. and mos preferably from about 600° C. to about 750° C. The pyrolysis temperature is the temperature of the gases inside at about the mid-point of the reaction zone.

The residence time of gases in the reaction zone is typically from about 0.5 to about 60 seconds, more preferably from about 2 seconds to about 20 seconds.

Through proper selection of operating conditions such as temperature and contact time, the process of the invention may be operated to produce predominantly mixtures of HFC-1234yf and HFC-1234ze from HFC-245eb. By predominantly is meant that the combined amount of HFC-1234yf and HFC-1234ze produced at a given single-pass conversion of HFC-245eb is greater than 50%, and preferably greater than 60%.

The reaction according to this invention can be conducted in the presence of one or more unreactive diluent gases, that is diluent gases that do not react under the pyrolysis conditions. Such unreactive diluent gases include the inert gases nitrogen, argon, and helium. Fluorocarbons that are stable under the pyrolysis conditions, for example, trifluoromethane and perfluorocarbons, may also be used as unreactive diluent gases. Of note are processes where the mole ratio of inert gas to $CF_3CH_2CF_3$ fed to the pyrolysis reactor is from about 5:1 to 1:1. Nitrogen is a preferred inert gas because of its comparatively low cost.

The reaction is preferably conducted at subatmospheric, or atmospheric total pressure. The reaction can be beneficially run under reduced total pressure (i.e., total pressure less than one atmosphere). Near atmospheric total pressure is preferred.

The reactor effluent after pyrolysis of HFC-245eb typically includes HF, $CHF_3$, $CH_2=CF_2$, $CF_3CF=CH_2$, $CF_3CH=CHF$, $CF_3CH=CF_2$ and small amounts of other byproducts and any unconverted $CF_3CHFCFH_2$.

Reaction products HFC-1234yf and HFC-1234ze and any unconverted HFC-245eb are recovered from the product leaving the reactor. The unconverted HFC-245eb can be recycled back to the reactor to produce additional HFC-1234yf and HFC-1234ze. In one embodiment of this invention, the unconverted HFC-245eb is recycled back to the reactor as it's azeotrope with HF. U.S. Patent Publication No. 2009/0264690, referenced above discloses an azeotrope of HF/HFC-245eb. U.S. Pat. No. 7,423,188 discloses an azeotrope of the E-isomer of HFC-1234ze and HF and a method to separate the HFC-1234ze from the azeotrope, and U.S. Pat. No. 7,476,771 discloses an azeotrope of HFC-1234yf and HF and a method to separate the HFC-1234yf from the azeotrope. HFC-1234ze may be recovered as a HF/HFC-1234ze azeotrope. Similarly, HFC-1234yf may be recovered as a HF/HFC-1234yf azeotrope. Pure HFC-1234ze and pure HFC-1234yf can be further recovered from their HF azeotropes by using methods similar to those described in U.S. Pat. No. 7,423,188 and U.S. Pat. No. 7,476,771, both of which are incorporated herein by reference.

The distillation columns, and their associated feed lines, effluent lines, and associated units used in applying the processes of this invention should be constructed of materials resistant to hydrogen fluoride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

Examples

General Procedure for Product Analysis

The following general procedure is illustrative of the method used for analyzing the products of fluorination reactions. Part of the total reactor effluent was sampled on-line for organic product analysis using a gas chromatograph equipped a mass selective detector (GC/MS). The gas chromatography utilized a 20 ft. (6.1 m) long×⅛ in. (0.32 cm) diameter tube containing Krytox® perfluorinated polyether on an inert carbon support. The helium flow was 30 mL/min ($5.0 \times 10^{-7}$ $m^3$/sec). Gas chromatographic conditions were 60° C. for an initial hold period of three minutes followed by temperature programming to 200° C. at a rate of 6° C./minute.

Legend 23 is $CHF_3$ 1132a is $CH_2=CF_2$

1225zc is $CF_3CH=CF_2$

1234yf is $CF_3CF=CH_2$

1234ze is E and Z-$CF_3CH=CHF$

245eb is $CF_3CHFCH_2F$

Examples

The reactor was a 9.5 inch (24.1 cm) long×0.50 inch (1.3 cm) outer diameter×0.35 inch (0.89 cm) inner diameter tubing with a wall thickness of 0.15 inch (3.8 mm) containing an internal gold lining. The thickness of the gold lining was 0.03 inch (0.08 cm). The reactor was heated with a ceramic band heater 5.7 inch long (14.5 cm)×1 inch outer diameter (2.5 cm) clamped to the outside. A dual control thermocouple, centered in the middle of the band heater between the outside of the reactor and the inside of the band heater was used to control and measure reactor temperature. To the reactor heated to various operating temperatures was fed 5 sccm ($8.33 \times 10^{-8}$ $m^3$/s) nitrogen and 2.37 ml per hr of liquid HFC-245eb that was vaporized before entering the reactor. The contact time was 60 seconds for all runs. The reactor effluent was analyzed by an in-line GC/MS. The product analysis in mole %, at various operating temperatures is summarized in Table 1.

TABLE 1

| Temp ° C. | Unknown | 23 | 1132a | 1234yf | E-1234ze | 1225ye | Z-1234ze | 245eb |
|---|---|---|---|---|---|---|---|---|
| 600 | 0.5 | 0.8 | 0.1 | 3.1 | 1.0 | ND | 0.2 | 94.3 |
| 650 | 1.9 | 4.7 | 1.0 | 5.9 | 2.3 | 0.3 | 0.8 | 83.1 |
| 700 | 4.3 | 17.4 | 5.1 | 16.7 | 8.5 | 1.8 | 3.7 | 42.5 |
| 750 | 7.7 | 24.6 | 7.9 | 28.0 | 14.8 | 3.4 | 6.6 | 6.9 |

ND = non-detectable

What is claimed is:

1. A process comprising pyrolyzing 1,1,1,2,3-pentafluoropropane to 2,3,3,3-tetrafluoropropene and 1,3,3,3-tetrafluoropropene wherein said pyrolyzing is carried out at a temperature from about 650° C. to about 900° C.

2. The process of claim 1 wherein said pyrolyzing is carried out to a single-pass conversion of said 1,1,1,2,3-pentafluoropropane of at least about 50%.

3. The process of claim 1 wherein said pyrolyzing is carried out at a temperature from about 650° C. to about 850° C.

4. The process of claim 1 wherein said pyrolyzing is carried out at a near atmospheric total pressure.

5. The process of claim 1 wherein said pyrolyzing is carried out for a reaction time of about 0.5 to 60 sec.

6. The process of claim 1 wherein said pyrolyzing is carried out in the presence of unreactive diluent gas.

7. The process of claim 6 wherein said unreactive diluent gas is selected from the group consisting of nitrogen, argon, helium.

8. The process of claim 1 wherein said pyrolyzing is carried out in a reactor which is substantially empty.

* * * * *